(12) United States Patent
McNeese et al.

(10) Patent No.: US 10,625,045 B2
(45) Date of Patent: Apr. 21, 2020

(54) EXPANDABLE INTRA-VENOUS CATHETER FOR A FASTER INTRA-VENOUS FLUID CHALLENGE

(71) Applicants: Marc A. McNeese, O'Fallon, IL (US); Shandra Y. McNeese, Belleville, IL (US)

(72) Inventors: Marc A. McNeese, O'Fallon, IL (US); Shandra Y. McNeese, Belleville, IL (US)

(*) Notice: Subject to any disclaimer, the term of this patent is extended or adjusted under 35 U.S.C. 154(b) by 373 days.

(21) Appl. No.: 15/726,245

(22) Filed: Oct. 5, 2017

(65) Prior Publication Data

US 2018/0093072 A1 Apr. 5, 2018

Related U.S. Application Data

(60) Provisional application No. 62/404,464, filed on Oct. 5, 2016.

(51) Int. Cl.
| | |
|---|---|
| *A61M 25/00* | (2006.01) |
| *A61M 25/06* | (2006.01) |
| *A61B 18/00* | (2006.01) |

(52) U.S. Cl.
CPC .... *A61M 25/0026* (2013.01); *A61M 25/0023* (2013.01); *A61M 25/0097* (2013.01); *A61M 25/0606* (2013.01); *A61B 2018/00214* (2013.01); *A61M 2025/004* (2013.01);
(Continued)

(58) Field of Classification Search
CPC .......... A61M 25/0026; A61M 25/0023; A61M 25/0606; A61M 2025/0024; A61M 2025/0036; A61M 2025/004; A61M 2025/0681; A61M 2025/0034; A61M 2025/0035; A61M 2025/0039; A61M 25/0028; A61M 25/0029; A61M 25/003; A61M 25/0032; A61M 2025/0031; A61M 2025/0037; A61M 2025/0025; A61M 1/285; A61M 25/0074; A61M 25/1006; A61M 25/1002; A61M 25/1011; A61M 2025/1043; A61M 2025/105;
(Continued)

(56) References Cited

U.S. PATENT DOCUMENTS

| | | | | |
|---|---|---|---|---|
| 4,141,364 | A | * | 2/1979 | Schultze ............... A61M 16/04 128/207.15 |
| 6,338,730 | B1 | * | 1/2002 | Bonutti ............. A61B 17/3439 604/239 |

(Continued)

*Primary Examiner* — Kami A Bosworth
*Assistant Examiner* — Leah J Swanson
(74) *Attorney, Agent, or Firm* — Charles McCloskey

(57) ABSTRACT

An expandable intra-venous catheter for a faster intra-venous fluid challenge combination has a needle with a tip and an opposite base, a block receiving the needle axially, an inflator port in the block and an opposite IV port 5 in the block, the IV port has fluid communication into the needle, at least three inflators deployed along the needle outwardly from the block, the inflator port has gaseous communication into the inflators, a sheath extending from the block over the inflators towards the tip, and an IV tube upon the needle and within the sheath. The catheter has a flat state and an expanded state. The catheter minimizes the need for multiple access points and raises the rate of access success upon a practitioner's initial IV attempt.

18 Claims, 5 Drawing Sheets

(52) U.S. Cl.
CPC ............ *A61M 2025/0024* (2013.01); *A61M 2025/0036* (2013.01); *A61M 2025/0681* (2013.01)

(58) Field of Classification Search
CPC .. A61M 2025/1061; A61M 2025/1072; A61M 2025/1081
See application file for complete search history.

(56) References Cited

U.S. PATENT DOCUMENTS

| | | | |
|---|---|---|---|
| 6,540,734 B1* | 4/2003 | Chiu ................ | A61M 25/1011 604/508 |
| 2006/0025749 A1* | 2/2006 | Moenning .......... | A61B 17/3417 604/506 |
| 2009/0005757 A1* | 1/2009 | Taber ................ | A61M 25/0071 604/523 |

* cited by examiner ature and time and time both

EXPANDABLE INTRA-VENOUS CATHETER FOR A FASTER INTRA-VENOUS FLUID CHALLENGE

CROSS-REFERENCE TO RELATED APPLICATION

This non-provisional application claims priority to provisional application No. 62/404,464 filed on Oct. 5, 2016, all of which are owned by a common inventor.

BACKGROUND OF THE INVENTION

The expandable intra-venous catheter for a faster intra-venous fluid challenge generally relates to catheters and more particularly to a fitting that expands. The present invention relates to intravenous needles that may adjust from a low volume to a high volume of flow without replacing one needle with a larger one. The invention relates to a needle of adjusting diameter readily used by medical staff.

The medical industry has a current problem that involves multiple access points for intra-venous fluids to be infused at a high or fast rate which requires the use of a larger bore needle or multiple points of access. The industry follows a current practice that involves the use of multiple sizes of intra-venous catheters, or IV catheters, needed in the delivery of certain lifesaving fluids, medications, and blood products. This current practice thus requires the need to access multiple IV sites during a patient's course of treatment.

Learning from the ancient practice of bloodletting and more modern practices of transfusions and blood typing, medicine has developed techniques for introducing fluids to a patient. The techniques involve connecting an exterior fluid source to the veins of a patient. The blood flow in the veins then distributes the added fluid into the body of a patient. The added fluid may range from saline fluid, medicinal fluid, up to blood products, and to blood itself. The added fluid generally brings therapeutic effect direct to the patient's bloodstream for prompt results. In select situations, the added fluid replaces other fluid lost from the patient because of trauma or surgery.

To add the fluid, medical staff find a vein upon a patient, typically in the arm or alternatively in the leg, apply a tourniquet to aid the visibility of the vein, and then insert a needle into the vein. The needle often has a socket attached to it for connection into a collection vial or an intravenous tube, or IV tube. The socket has one of select sizes and shares compatibility with existing IV tube systems and their abundant fittings. The fittings allow for delivery of added fluid to the patient and to regulate that delivery as to volumetric flow rate.

DESCRIPTION OF THE PRIOR ART

Existing needles generally have one of select sizes usually measured in gauge though also corresponding to millimeters or inches from time to time. Usually medical staff inserts one needle of one size and that needle remains in the vein of a patient. A same size needle works well for delivery of added fluid until a change must occur to that delivery.

A traumatic event or indication for greater delivery of added fluid may call for a rapid, instantaneous, or abrupt increase, in size of needle. Presently medical staff faced with that situation, removes a needle from a patient then follows the insertion procedure with a larger diameter needle. The medical staff repeats the vein acquisition and then vein puncturing procedure as before. And time and effort both endure repetition while the patient has another hole placed into him. In some medical situations, the medical staff must do this fast, almost too fast.

Medical staff must select the larger needle, remove the smaller needle, emplace the larger needle in the patient, and then reconnect that larger needle to the exterior fluid source. Skilled staff may accomplish these tasks in a timely manner. In the urgent conditions of a trauma bay or a cardiac operating room, ordinary staff may risk patient safety.

The present invention overcomes the disadvantages of the prior art and provides a expandable intra-venous catheter for a faster intra-venous fluid challenge that eliminates swapping of large for small needles, reinsertion of needles, and lessens staff error risk. Furthermore, the new and improved expandable intra-venous catheter for a faster intra-venous fluid challenge makes it possible for abruptly increasing or decrease the volume of added fluid delivered to a patient through an IV line.

SUMMARY OF THE INVENTION

Generally, the present invention provides an expandable intra-venous catheter for a faster intra-venous fluid challenge for patients under the care of medical staff. Though the word patient is used that also includes veterinary patients and though the phrase medical staff is used that also includes veterinary staff, first responders, and other users of IV lines. The present invention has a needle with a tip and an opposite base, a block receiving the needle axially, an inflator port in the block and an opposite IV port in the block, the IV port has fluid communication into the needle, at least three inflators deployed along the needle outwardly from the block, the inflator port has gaseous communication into the inflators, a sheath extending from the block over the inflators towards the tip, and an IV tube upon the needle and within the sheath. The present invention has a flat state and an expanded state.

The present invention conceivably reverses the process by accessing a vein of a patient with a small bore needle, or catheter, then expanding the lumen of the catheter after venous access has been obtained. This process allows for an adjustable IV catheter bore but with use of a small needle at the access point, thus allowing for a higher and faster fluid infusion rate without the use of multiple access points. The present invention differs from the prior art. The present invention minimizes or even eliminates the need for multiple sizes of IV catheters used in the current practices of the industry to sustain rapid infusion of fluids and blood products. The present invention further improves upon existing technology. The existing technology and practices require multiple access points which require multiple venipunctures that are uncomfortable and displeasing to a patient. These practices additionally consume time and labor during traumatic lifesaving events. The present invention minimizes the need for multiple access points and additionally provides a higher rate of access success upon a practitioner's initial IV insertion attempt.

There has thus been outlined, rather broadly, the more important features of the invention in order that the detailed description thereof that follows may be better understood and that the present contribution to the art may be better appreciated. The present invention also includes minimizing the need for multiple access points in addition to a higher rate of access success upon a practitioner's initial IV access attempt, passages through the block for fluidic and gaseous communication without contamination of one by the other, vents upon the needle in communication with vents through the IV tube and the sheath, a shoulder outwardly from the block, and a sheath outwardly from the shoulder. As stated above, the current problem within the industry involves multiple access points for intra-venous fluids to be infused at a high or fast rate which requires the use of a larger bore needle or multiple points of access. The present invention solves that problem. The present invention ensures IV access without the challenges and difficulties associated with missed attempts when large bore IV's are necessary during critical moments of patient care and in addition to pre-hospital settings as performed by the EMS or other first responder. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide an expandable intra-venous catheter for a faster intra-venous fluid challenge that provides consistent delivery with a macro gauge venous cannulation platform with a micro gauge profile.

Another object is to provide such an expandable intra-venous catheter for a faster intra-venous fluid challenge that promotes peripheral access.

Another object is to provide such an expandable intra-venous catheter for a faster intra-venous fluid challenge that lessens the challenge of fluid replacement and resuscitation in critical and emergent situations.

Another object is to provide such an expandable intra-venous catheter for a faster intra-venous fluid challenge that prompts immediate access in large bore situations.

Another object is to provide such an expandable intra-venous catheter for a faster intra-venous fluid challenge that raises the large bore success percentages.

Another object is to provide such an expandable intra-venous catheter for a faster intra-venous fluid challenge that may be utilized in every aspect of IV therapy.

Another object is to provide such an expandable intra-venous catheter for a faster intra-venous fluid challenge that provides logic in the sense of IV access in respect to anatomical location prior to the decision to dilate to a larger gauge.

Another object is to provide such an expandable intra-venous catheter for a faster intra-venous fluid challenge that introduces large gauge capacity in a small gauge profile.

Another object is to provide such an expandable intra-venous catheter for a faster intra-venous fluid challenge that has multiple points of flow.

Another object is to provide such an expandable intra-venous catheter for a faster intra-venous fluid challenge that has variable diameters of flow.

Another object is to provide such an expandable intra-venous catheter for a faster intra-venous fluid challenge that provides multiple fluid paths.

Another object is to provide such an expandable intra-venous catheter for a faster intra-venous fluid challenge that has a low cost of manufacturing so the purchasing physicians, nurses, practices, practice groups, hospitals, medical facilities, veterinary facilities, and organizations can readily buy the invention through stores and supply sources.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there is illustrated and described a preferred embodiment of the invention.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
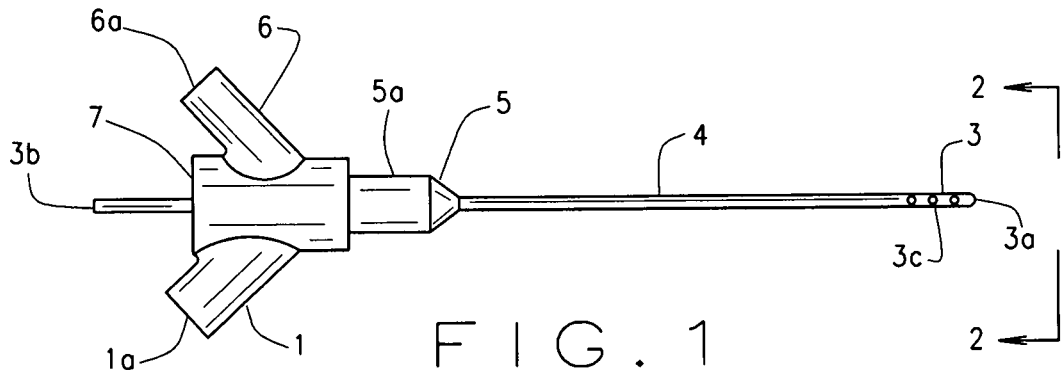
FIG. 1 shows a top view of the preferred embodiment of the present invention.

The present invention overcomes the prior art limitations by providing an expandable intra-venous catheter for a faster intra-venous fluid challenge especially during critical or emergent situations and sees general use by nurses, doctors, clinicians, technicians, and related staff who engage in fluid replacement of patients.

A practitioner, or medical staff, follows a procedure or method of use for the present invention. The method includes these steps. First, gathering traditional material necessary for the starting of an IV catheter. These items have traditional name of an IV starter kit that has a tourniquet, alcohol prep pad, tape, 2×2 gauge pad, and a clear site cover adhesive dressing. These items fit into a single one time use sterile packet. Second, incorporating the present invention with an appropriate needle. The present invention has a 25 or 27 gauge needle that has expansion capabilities ranging from 27 to 14 gauges of diameter. The present invention has a durable, elastic, non-latex, hypoallergenic construction that has expansion and recoil properties. Third, identifying an extremity for deployment. The medical staff selects an extremity to receive an IV and prepares a chosen area as traditionally performed in IV start procedures including applying a tourniquet above the access or puncture site. Fourth, retracting of the needle. After completing IV catheter insertion and obtaining venous access, confirmed by a blood flash in the needle chamber, the needle is retracted but still attached to the hub of the catheter. The tourniquet remains in a tight position until the desired gauge of the catheter is achieve by a dialing mechanism attached to the catheter. Upon achieving the desired gauge, medical staff releases the tourniquet. The IV is now ready for securement to existing IV tubing or a designated IV capping system in accordance with a respective facility's standard of practice. And fifth, adjusting catheter gauge. To remove or to adjust to an increase in catheter gauge, medical staff reapplies a tourniquet to obtain venous dilation prior to the adjustment for the purposes of patient comfort.

The above first through third steps are traditional procedures necessary for the insertion of typical IVs in a standard way. The fourth step shows the present invention and its true innovation. The fifth step may be eliminated or modified in emergent situations, those when time is of the essence. As a reminder, a fluid challenge involves the rapid administration of a bolus of fluid in critically ill, generally haemodynamically unstable patients who require rapid correction of an hypovolaemic state. It is essential that an assessment of response to the fluid challenge follows its administration.

The present invention can be used and characterized similar to other IV access devices. The present invention though has a critical difference where only one size is necessary for a facility to stock as opposed to present practices of stocking multiple sizes in facilities across the nation.

In the preferred embodiment of the present invention, an expandable intra-venous catheter, appears with reference to the drawings in FIG. 1. FIG. 1 has a top view of the invention in a deflated state. The inflated state appears later starting in FIG. 9. The invention has a needle 3 generally elongated, slender, and hollow. The needle has a pointed tip 3a and an opposite base 3b. Proximate the tip, the needle has a plurality of vents 3c generally spaced in a pattern of a short length inwardly from the tip. Away from the tip and closer towards the base, the invention has a block 7. The block has a generally cylindrical form though appearing rectangular in this plan, top view. The block has a diameter much greater than the needle by at least three times the diameter of the needle. Though the term diameter of the needle is used, that also includes the term gauge. The block has a length generally more than its diameter and at least five times the diameter of the needle. The block has an aft face from which the base 3b extends and an opposite fore face from which a shoulder 5a extends in the direction of the tip. The shoulder has a lesser diameter than the block and the shoulder's diameter generally steps inwardly from that of the block as shown. Forwardly from the shoulder, that is, inwardly from the block towards the tip, a sheath 5 tapers inwardly in a generally conical shape. The sheath nearly reaches the exterior of the needle 3. Towards the fore face, the block has an IV port 6 extending at a rearward skew from the axis of the needle 3a, The IV port 6 makes an acute angle with the base 3b as shown. The IV port has an opening 6a that receives another IV line or other tubular connection as utilized in the medical industry. The IV port has a cylindrical form with its diameter. Opposite the IV port, the block has an inflator port 1. The inflator port also extends at a rearward skew from the axis of the needle 3a but at a mirror image from that of the IV port 6. The inflator port 1 makes an acute angle with the base 3b as shown. The inflator port 1 has its opening 1a that receives an air line or other tubular connection as utilized in the medical industry or other industries that have inflation. The inflator port also has a cylindrical form with its diameter though slightly larger than the diameter of the IV port 6. The inflator port has less exposed length outwardly from the aft face compared to the IV port. The inflator port may receive a separate cap for physical blocking of the opening.

Having described the block 7 and nearby structure, the sheath 5 approaches the needle 3. The sheath merges with an IV tube 4 that extends for the majority of the length of the needle. The IV tube encircles the needle and has a snug fit upon it as shown. The IV tube also has its vents that communicate with the vents 3c of the needle.

Figure 2:
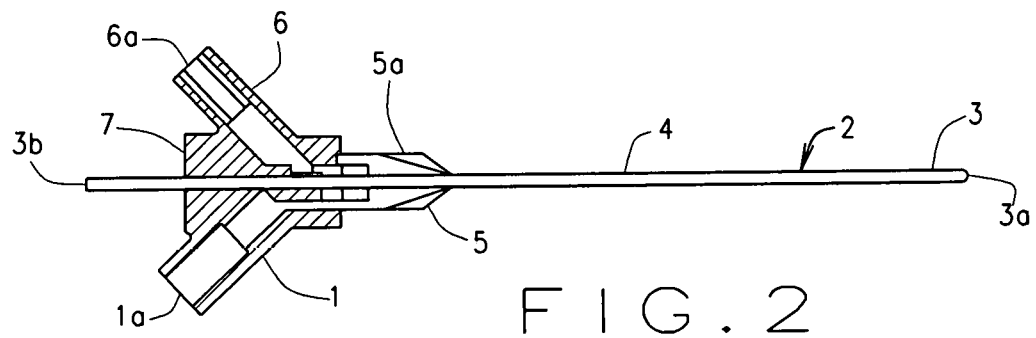
FIG. 2 provides a section view of the preferred embodiment of the present invention.
Figure 3:
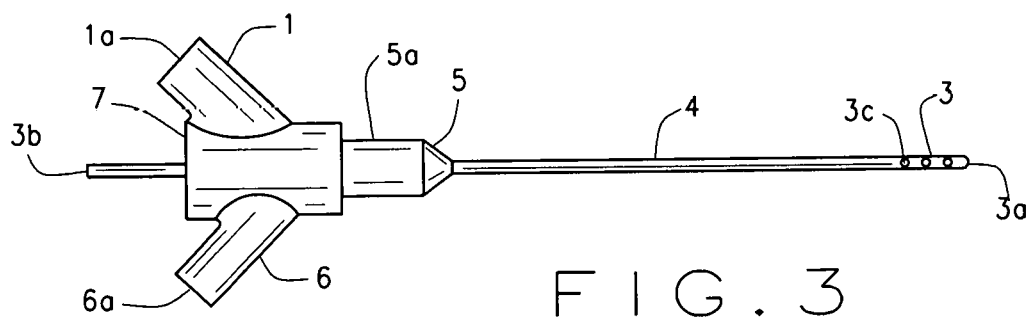
FIG. 3 illustrates a bottom view of the preferred embodiment of the present invention.

Referring now to FIG. 2, the invention appears in a section view primarily showing the internal passages within the block 7. The IV port 6 has its hollow form that communicates into the block inwardly from the aft face towards the fore face of the block and radially inward from outwardly of the needle to near the needle 3. The opening 6a of the IV port has fluid communication into the needle 3 within the block where the opening 6a reaches the center of the block. Then the inflator port 1 also has its hollow form that communicates into the block inwardly from the aft face towards the fore face of the block and radially inward from outwardly of the needle to adjacent to the needle 3. The opening 1a of the inflator port has fluid communication into the block through a passage mutually parallel and spaced apart from the needle 3 within the block where the opening 1a approaches the center of the block. This passage extends for at least two needle diameters and enters within the shoulder 5a. The passage provides communication for air, other gasses, or fluids into the sheath 5. a Turning the invention over, FIG. 3 shows a bottom view of the invention generally opposite that of FIG. 1. In this view, the inflator port 1 appears upwardly and the IV port 6 appears downwardly. Both ports extend outwardly from the block 7 as before while the base 3b of the needle extends rearwardly form the aft face of the block. The needle 3 continues through the block 7 from the base and passes through the shoulder 5a and within the sheath 5. The IV tube 4 then encircles the needle 3 for most of its length. The IV tube 4 has vents that communicate with the vents 3c of the needle shown near the tip 3a.

Figure 4:
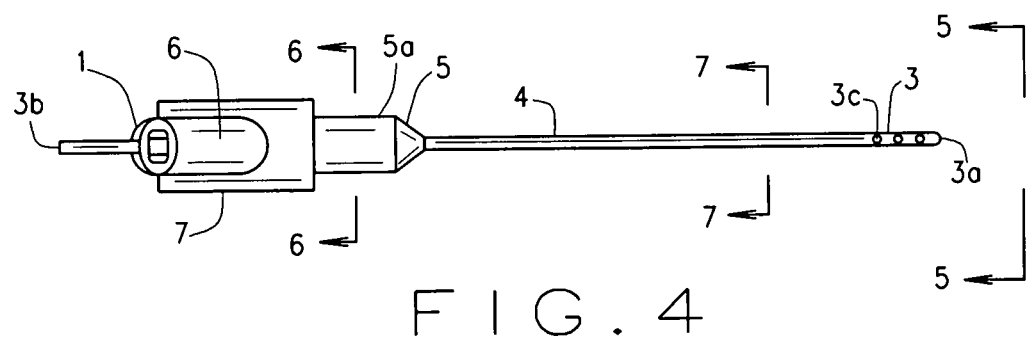
FIG. 4 describes a side elevation view of the preferred embodiment of the present invention.

Next, FIG. 4 shows a side view of the expandable intra-venous catheter with the IV port 6 towards the foreground. The IV port extends into the plane of the figure at a skew and reaches the block 7. Opposite the IV port, the inflator port 1 has its slightly larger diameter shown before it approaches the block 7 at a skew from the background of the figure. Between the IV port and the inflator port, the base 3b of the needle extends inwardly to the fore face of the block. The block continues its cylindrical form inwardly and then its diameter steps inwardly to form the shoulder 5a. The shoulder has its length as shown along the needle but less than the length of the block. The shoulder then starts another narrowing of the invention with the sheath 5. The sheath has its conical form tapering inwardly to the IV tube 4 that encircles the remainder of the needle. The needle then extends for most of its slender, elongated form displaying its vents 3c towards its tip 3a. The tip has a sharpened point for use during insertion to a patient by medical staff.

Figure 5:
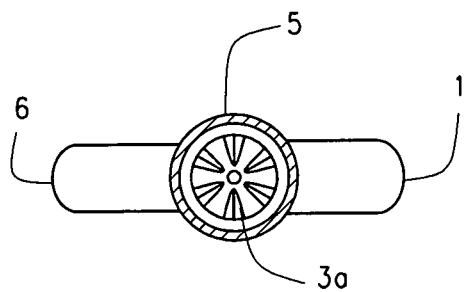
FIG. 5 shows a front view of the preferred embodiment of the present invention.

FIG. 5 shows a front view with the tip 3a of the needle 3 centered in the figure. The needle within the IV tube both extends into the plane of the figure and join to the sheath 5. The sheath then expands outwardly to the shoulder 5a with the remainder of the block behind it. In this figure, the IV port 6 extends outwardly to the left and the inflator port 1 extends outwardly to the right. The IV port 6 has a lesser diameter than that of the inflator port 1.

Figure 6:
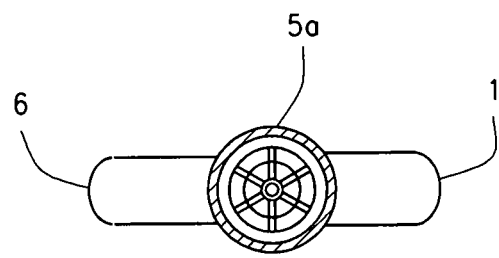
FIG. 6 illustrates a section view of the preferred embodiment of the present invention.

Then FIG. 6 has a section view through the shoulder 5a. The shoulder provides a major passageway that admits an inflating mechanism here shown as six radial lines stiffening a perimeter ring. The mechanism divides the air, gas, or fluid flow form the inflator port 1 into the IV tube 4.

Figure 7:
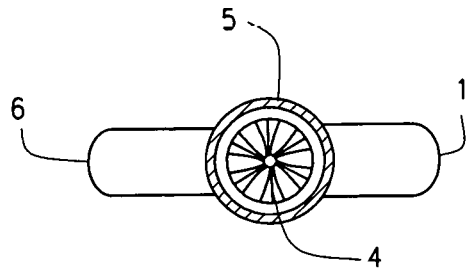
FIG. 7 provides a section view of the preferred embodiment of the present invention.

In FIG. 7, a section view through the IV tube 4 and needle 3 shows their concentric positioning. The needle within the IV tube continues out of the plane of the figure towards the reader. Into the plane of the figure, the needle within the IV tube has the IV tube merge into the sheath 5 shown in the foreground. The IV tube encircles the needle in a pattern.

Figure 8:
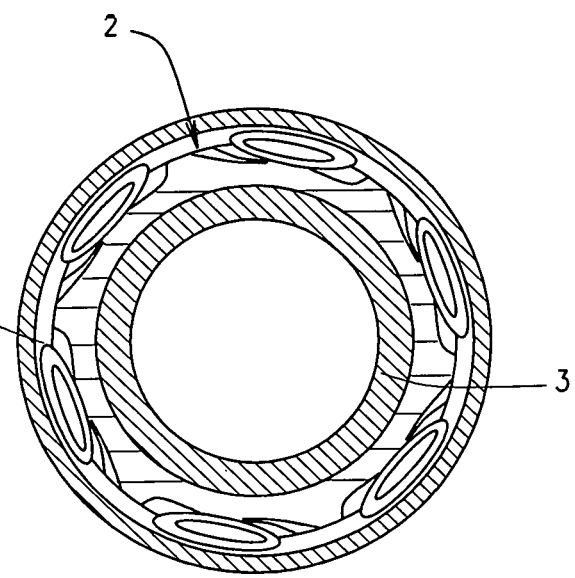
FIG. 8 shows a detailed sectional view of the preferred embodiment of the present invention.

The pattern appears more particularly in FIG. 8. FIG. 8 shows a detailed sectional view through the IV tube 4 and the needle 3 along the length of the needle between the tip and the shoulder. The needle 3 has its generally hollow form with an axial opening for fluid flow. The opening has a wall that surrounds it forming the slender, elongated structure of the needle. The needle has an inner diameter and an outer diameter separated by the wall thickness. The inner diameter, the outer diameter, and the wall thickness may be express in inches, centimeter, gauge, and the like. The needle also has an exterior surface generally opposite and outwardly from the opening. Upon the exterior surface, the needle has a plurality of inflators 2 in a regular spacing around the exterior surface. The plurality has a minimum number of three while this figure shows six inflators. The inflators extend along the exterior surface of the needle from proximate the tip 3a rearwardly to the sheath. Inwardly from the inflators and along the exterior surface, the invention has the IV tube 4. As before, the IV tube encircles the needle. Outwardly from the inflators, the invention has its sheath encasing it.

Figure 9:
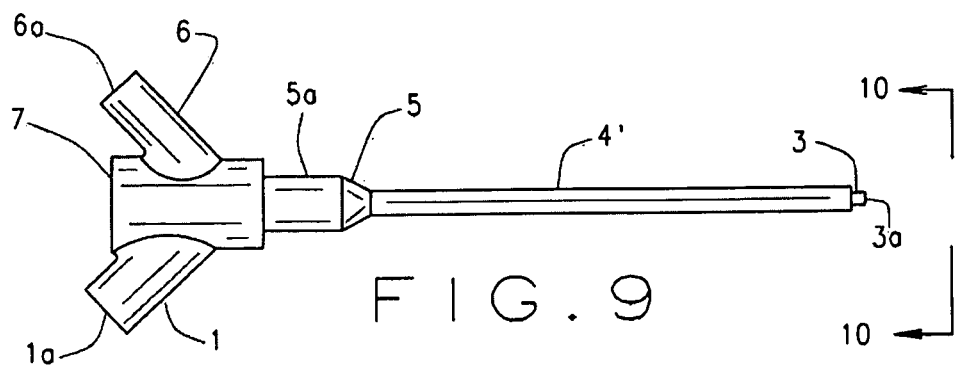
FIG. 9 shows a top view of the preferred embodiment of the present invention when inflated.

The preceding description shows the invention of the expandable intra-venous catheter when not inflated, that is, in compact form. In this form, the sheath, the IV tube, and the inflators compress upon the needle for most of its length. Turning now to FIG. 9, the invention appears in its inflated state in a top plan view. The invention has its needle 3 of elongated, slender, and hollow form as before with a pointed tip 3a and an opposite base 3b. Near the tip, the plurality of vents 3c communicate with similar vents in the IV tube. The vents of the IV tube have registration with the vents 3c of the needle. Away from the tip, the invention has its block 7 though the base 3b of the needle has retracted inwardly to the aft face of the block. The block has its previous generally cylindrical form and a diameter much greater than the needle. The block also has its length generally more than its diameter and at least five times the diameter of the needle. The block has its aft face generally away from the tip 3a and that contains the base 3b and an opposite fore face that merges with the shoulder 5a in the direction of the tip. The shoulder has a lesser diameter than the block and generally steps inwardly in diameter from that of the block. Inwardly from the block towards the tip, the sheath 5 tapers inwardly in its conical form as before. The sheath nearly reaches the exterior of the needle 3 while it merges with the IV tube 4'. Towards the fore face, the block has its IV port 6 extending at a rearward skew from the axis of the needle 3a and it makes an acute angle with the aft face. The IV port has its opening 6a that receives another IV line and has its cylindrical form with its diameter. Opposite the IV port, the block has the inflator port 1 that also extends at a rearward skew from the axis of the needle 3a but at a mirror image from that of the IV port 6. The inflator port 1 makes an acute angle with the aft face as shown and has it opening 1a that receives an air line. The inflator port also has its cylindrical form with its diameter slightly more than that of the IV port 6.

Turning away from the block 7, the sheath 5 approaches the needle 3. The sheath merges with an IV tube 4' that extends for most of the length of the needle. The IV tube encircles the needle in a snug fit upon it as shown. The IV tube also has its vents that communicate with the vents 3c of the needle. Differing from FIG. 1, the IV tube here as at 4' has an inflated appearance of greater diameter than in FIG. 1.

Figure 10:
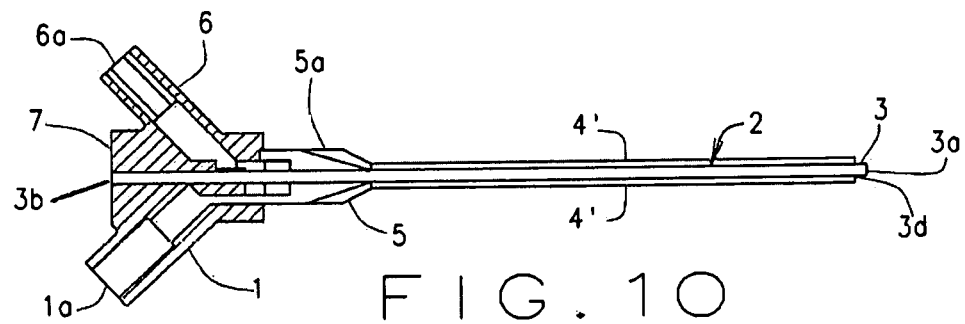
FIG. 10 provides a section view of the preferred embodiment when inflated.
Figure 16:
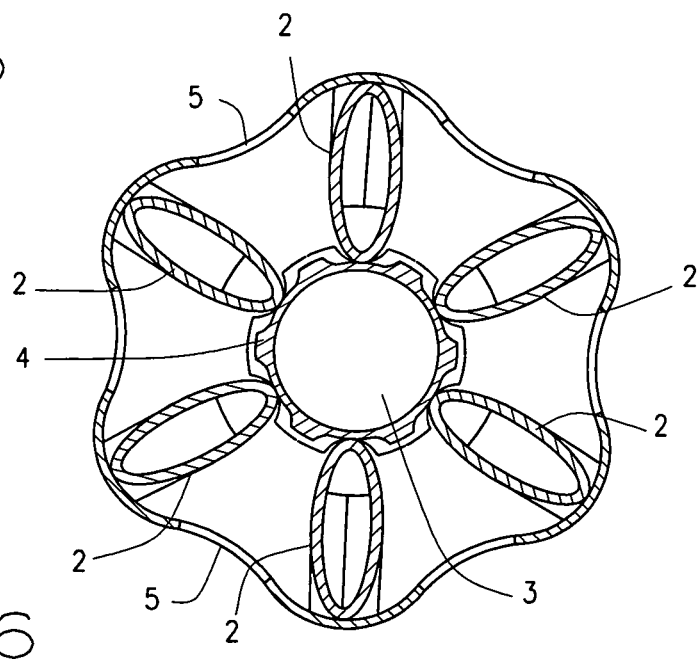
FIG. 16 shows a detailed sectional view of the preferred embodiment when inflated.

Moving to FIG. 10, the invention appears in a section view showing the internal passages within the block 7, inflators 2 extending along the needle 3, and the inflators creating a head 3d. As before, the IV port 6 has a hollow form communicating into the block inwardly from the aft face towards the fore face of the block and radially inward from outwardly of the needle to near the needle 3. The IV port opening 6a has fluid communication into the needle 3 within the block where the opening 6a reaches the center of the block. Then the inflator port 1 also has its hollow form that communicates into the block inwardly from the aft face towards the fore face of the block and radially inward from outwardly of the needle to adjacent to the needle 3. The opening 1a of the inflator port has fluid communication into the block through a passage mutually parallel and spaced apart from the needle 3 within the block where the opening 1a approaches the center of the block. This passage extends for at least two needle diameters and enters within the shoulder 5a. The passage provides communication for air, other gasses, or fluids into the sheath 5. Inside of the sheath, the passage admits air into a plurality of inflators 2. As a section view, this figure shows two inflators spaced apart and around the needle. FIG. 16 later shows additional inflators. Here, the two inflators extend along the needle 3 from the sheath's merge with the shoulder outwardly from the block towards the tip 3a. The inflators end slightly inwardly from the tip and form a head 3d. The head shows a step inwardly in diameter from the inflators to the needle itself. The inflators retain air within them and enlarge the sheath for nearly the length of the needle.

Figure 11:
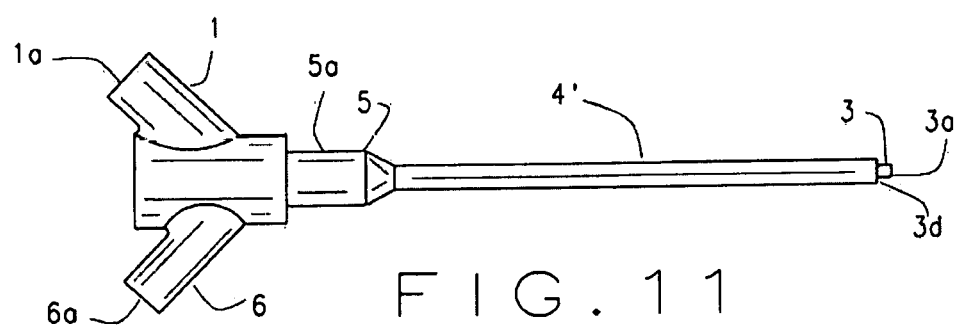
FIG. 11 illustrates a bottom view of the preferred embodiment when inflated.

Turning the invention over, FIG. 11 again shows a bottom view of the invention generally opposite that of FIG. 9. Here, the inflator port 1 appears upwardly and the IV port 6 opposite it. Both ports extend outwardly from the block 7 as before while the base 3b of the needle remains flush with the aft face of the block. The needle 3 continues through the block 7 from the base and passes through the shoulder 5a and within the sheath 5. The IV tube 4' then encircles the needle 3 for most of its length. The IV tube 4' has vents that communicate with the vents 3c of the needle shown near the tip 3a. The inflators 2 remain outwardly from the IV tube 4' and within the sheath 5. The inflators when inflated as shown present a wider form of the needle and the head 3d proximate the tip.

Figure 12:
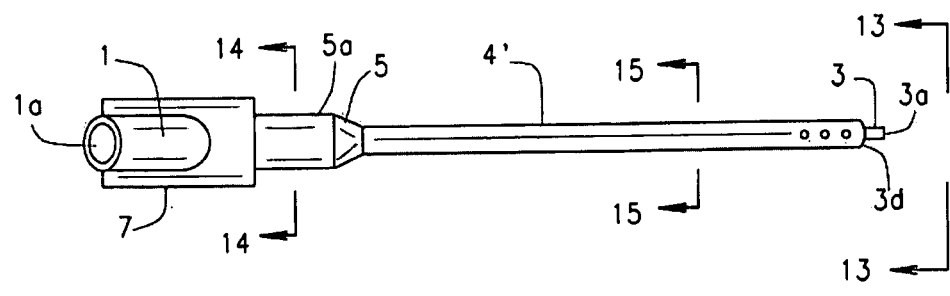
FIG. 12 describes a side elevation view preferred embodiment when inflated.

Next, FIG. 12 shows a side view of the expandable intra-venous catheter with the inflator port 1 towards the foreground and the inflators 2 full of air therein showing a wider form of the needle. The inflator port extends into the plane of the figure at a skew and reaches the block 7. Opposite the inflator port, the IV port has its slightly less diameter and thus appears concealed by the inflator port as it approaches the block at a skew from the background of the figure. Between the IV port and the inflator port, the base of the needle remains flush with the aft face of the block. The block continues its cylindrical form inwardly and then its diameter steps inwardly to form the shoulder 5a. The shoulder has its length as shown along the needle but less than the length of the block. The shoulder then starts another narrowing of the invention to the sheath 5. The sheath has its conical form tapering inwardly similar to before for less internal angle to the inflated inflators within the sheath and around the IV tube 4' that encircles the remainder of the needle. The needle then extends for most of its slender, elongated form displaying its vents 3c towards its tip 3a. The vents 3c communicate with similar vents in the sheath as shown. The inflators cooperating with the sheath near the tip present the head 3d that steps inwardly in diameter from the enlarged form of the needle to the actual needle.

Figure 13:
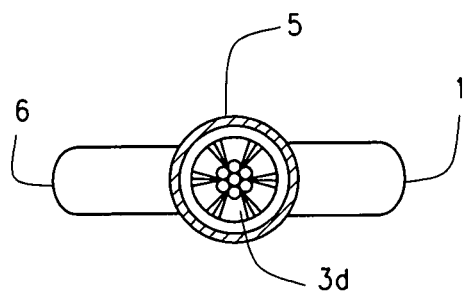
FIG. 13 shows a section view of the preferred embodiment when inflated.

FIG. 13 shows a front view with the head 3d shown outwardly of the needle's tip 3a. As before, the needle fits inside of the inflators and the IV tube then both extend into the plane of the figure and join to the sheath 5. The sheath then expands outwardly to the shoulder 5a with the remainder of the block behind it. In this figure, the IV port 6 extends outwardly to the left and the inflator port 1 extends outwardly to the right. The IV port 6 has a lesser diameter than that of the inflator port 1.

Figure 14:
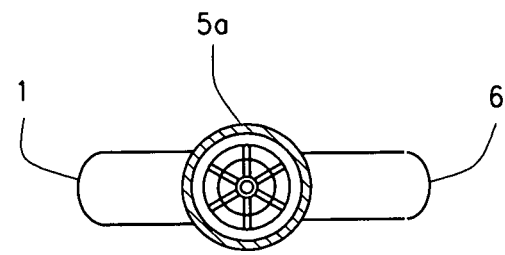
FIG. 14 illustrates a section view of the preferred embodiment when inflated.

Then FIG. 14 has a section view through the shoulder 5a. As above, the shoulder has a major passageway admitting the inflating mechanism within it. The inflating mechanism here shown has six radial lines, generally vanes upon edge, that stiffen a perimeter ring. The vanes of the mechanism divide the air, gas, or fluid flow form the inflator port 1 into the IV tube 4'.

Figure 15:
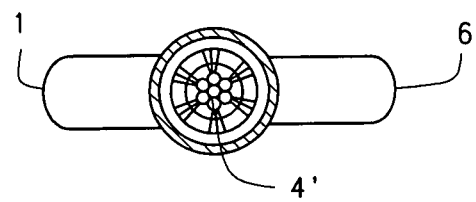
FIG. 15 provides a section view of the preferred embodiment when inflated.

Over in FIG. 15, a section view through the IV tube 4' and needle 3 shows their mutually concentric positioning. The needle within the IV tube continues out of the plane of the figure towards the reader. Into the plane of the figure, the needle within the IV tube has the IV tube merge into the sheath 5 shown in the foreground. The IV tube encircles the needle in a pattern, inflated for usage.

The inflated pattern appears more particularly in FIG. 16. FIG. 16 shows a detailed sectional view through the IV tube 4' and the needle 3 along the length of the needle between the tip and the shoulder. The needle 3 has its generally hollow form with an axial opening for fluid flow. The needle's opening has a wall that surrounds it forming the slender, elongated structure of the needle. The needle has its inner diameter and outer diameter separated by the wall thickness as before. The needle also has an exterior surface generally opposite and outwardly from the opening. Upon the exterior surface, the needle has a plurality of inflators 2 in a regular spacing around the exterior surface. The plurality has a minimum number of three while this figure shows six inflators. The inflators extend along the exterior surface of the needle from proximate the tip 3a rearwardly to the sheath.

Previously in FIG. 8, the inflators appeared flat and compressed by the sheath against the tube 4 and the needle 3. FIG. 16 though shows the invention inflated for use. Here the inflators have air, other gas, or other fluid introduced into them. The inflators then expand radially outwardly from the IV tube 4' as shown. The inflators have a generally elliptical cross section with the major axis of the ellipse oriented radially outward while the minor axis of the ellipse has a tangential orientation to the IV tube 4'. The inflators have a length of major axis at least fifty percent of the diameter of the needle and a length of minor axis less than fifty percent of the needle's diameter. The inflators have an equiangular position around the tube so that upon using six inflators each inflator has another inflator opposite it. Upon using three inflators, the inflators also have an equiangular position but no inflator has another inflator opposite it. The inflators fit within the sheath 5 and the IV tube 4'. Shown here, the sheath stretches and elongates to accommodate the increase in diameter of the invention from the inflated inflators. The sheath spans between adjacent inflators and does not contact the IV tube 4' when the invention is in an expanded state. Opposite the sheath, each inflator contacts the IV tube 4' that has the needle 3 within it.

Figure 17:
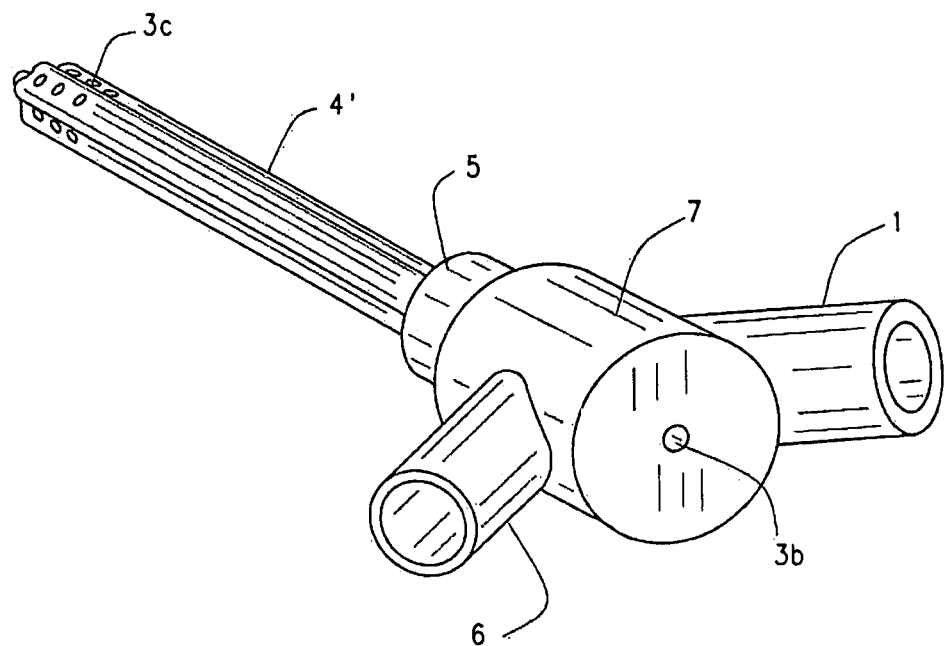
FIG. 17 shows a rear perspective view of the preferred embodiment when inflated; and, FIG. 18 shows a front perspective view of the preferred embodiment when inflated.

The invention appears as a medical staff would insert it in FIG. 17. The block 7 has its general cylindrical from with the aft face in the foreground and the base 3b centered therein. Outwardly from the block and the aft face, the invention has the IV port 6 shown to the left and the inflator port 1 behind the block towards the right. The block continues inwardly and steps inwardly to the shoulder which then extends and tapers to the sheath 5. The sheath then merges with the expanded IV tube 4'. The inflators, not shown, have the sheath at its widest shape in the inflated state shown here. The IV tube 4' extends outwardly from the sheath for nearly the length of the needle. Outwardly from the sheath and the block, the IV tube 4' has vents that communicate with the vents 3c of the needle.

Figure 18:
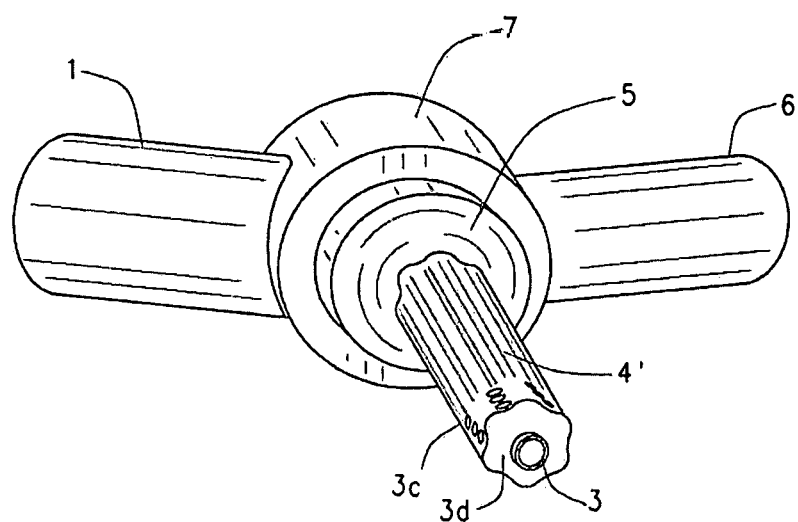

And turning the invention, FIG. 18 shows the expandable intra-venous catheter as a patient may see it during insertion, that is, needle tip first. The needle tip has the head 3d shown outwardly of the tip while the tip remains open for fluid communication through the needle 3. Rearwardly from the head, the IV tube 4' has its vents that communicate with those 3c of the needle interiorly. The IV tube 4' extends rearwardly and joins with the sheath 5 here shown widening outwardly toward the shoulder and then the shoulder steps outwardly to the diameter of the block 7. The block has the inflator port 1 to the left and the IV port 6 to the right.

From the aforementioned description, an expandable intra-venous catheter for a faster intra-venous fluid challenge has been described. The expandable intra-venous catheter for a faster intra-venous fluid challenge is uniquely capable of expanding its effective bore from one insertion of a needle. The expandable intra-venous catheter for a faster intra-venous fluid challenge has select components that inflate and create additional passages for greater fluid volume than the inserted needle. The expandable intra-venous catheter for a faster intra-venous fluid challenge, and its various components may be manufactured from many materials, including but not limited to, cotton, wool, polyester, steel, aluminum, brass, bronze, polymers, high density polyethylene, polypropylene, ferrous and non-ferrous metals, their alloys, and composites. More particularly as described above in the second step, the present invention has fabrication and construction within the concept of an expandable, webbed, durable, non-latex, and hypoallergenic material along with the catheter expansion dial or component. This is necessary to ensure the product readiness and patient safety during its usage. The catheter delivery over a 25 or 27 gauge needle is paramount in the access success rate and the patient's comfort and satisfaction. In an alternate embodiment, a dialing mechanism for catheter expansion could be replaced with an expansion balloon that is activated by a syringe to fill the balloon within the inner lumen of the catheter. This alternate embodiment operates to increase or to decrease the gauge of the catheter.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

While the present invention has description above of its preferred embodiment, it will be understood that it is not intended to limit the invention to these embodiments. Instead, it is intended to cover all alternatives, modifications and equivalents as may be included within the spirit and scope of the present invention as defined by the appended claims.

We claim:

1. A medical device comprising: a hollow needle with a tip and an opposite base; a block receiving said needle axially therein, an inflator port in said block and an opposite intra-venous port in said block; at least three inflators along said needle extending outwardly from said block towards said tip; said intra-venous port having fluid communication into said needle and said inflator port having gaseous communication into said inflators; a sheath extending from said block over said inflators towards said tip; and, an intra-venous tube concentric and coaxial with said needle and within said sheath; wherein said device transitions from a flat state having said inflators flat and adjacent to said intra-venous tube to an expanded state having said inflators enlarged radially outwardly from said intra-venous tube.

2. The medical device of claim 1 further comprising: said block having a generally cylindrical form, a diameter, and a length perpendicular to the diameter, a shoulder having a diameter lesser than that of said block and a length lesser than that of said block, said shoulder being coaxial with said block, said shoulder located opposite said inflator port and said intra-venous port, and said shoulder having fluid communication to said needle; and, said sheath having a conical portion fitting upon said shoulder.

3. The medical device of claim 2 further comprising:
said sheath extending outwardly from said shoulder upon said inflators to near said tip.

4. The medical device of claim 3 further comprising:
said sheath forming a head slightly inwardly from said tip;
said needle having a plurality of vents proximate said tip;
said sheath having a plurality of vents in registration with the plurality of vents of said needle.

5. The medical device of claim 1 further comprising:
each of said inflators having an elliptical cross section when said device is in the expanded state, the elliptical cross section having a major axis and a minor axis of lesser length than the major axis;
each of said inflators having its major axis oriented radially outwardly from said intra-venous tube; and,
said sheath enlarging and encasing said inflators when said device is in the expanded state.

6. The medical device of claim 5 wherein said inflators have an equiangular spacing around said intra-venous tube.

7. The medical device of claim 6 further comprising:
a passage between each pair of adjacent inflators wherein said passage forms when said device is in the expanded state;
each of said passages having an equiangular spacing around said intra-venous tube; and,
each of said passages adapted to increase fluid flow rate from that of said needle.

8. The medical device of claim 7 further comprising:
each of said inflators joining to said intra-venous tube at one end of the major axis and to said sheath at the other end of the major axis.

9. The medical device of claim 8 further comprising:
six of said inflators and six of said passages.

10. An expandable catheter that increases fluid flow rate comprising: a block having a generally cylindrical form, a diameter, and a length perpendicular to the diameter, an inflator port in said block and an opposite intra-venous port in said block, a shoulder having a diameter lesser than that of said block and a length lesser than that of said block, said shoulder being coaxial with said block, said shoulder located opposite said inflator port and said intra-venous port; a hollow needle with a tip and an opposite base, said needle extending axially through said block and outwardly from said shoulder; an intra-venous tube concentric and coaxial with said needle and outwardly from said shoulder; at least three inflators along said needle extending outwardly from said shoulder towards said tip, said inflators having an equiangular spacing around said intra-venous tube; a sheath extending from said shoulder over said inflators towards said tip and outwardly from said intra-venous tube, said sheath having a conical portion fitting upon said shoulder; said intra-venous port having fluid communication into said needle, said inflator port having gaseous communication into said inflators, and said shoulder having fluid communication to said needle; said intra-venous tube being within said inflators and within said sheath; and, wherein said catheter transitions from a flat state having said inflators flat and adjacent to said intra-venous tube to an expanded state having said inflators enlarged radially outwardly from said intra-venous tube.

11. The expandable catheter of claim 10 further comprising:
each of said inflators having an elongated, hollow, slender form, a flat cross section when said catheter is the flat state and an elliptical cross section when said catheter is in the expanded state, the elliptical cross section having a major axis and a minor axis of lesser length than the major axis;
each of said inflators having its major axis oriented radially outwardly from said intra-venous tube; and,
said sheath enlarging and encasing said inflators when said catheter is in the expanded state.

12. The expandable catheter of claim 11 further comprising:
each of said inflators joining to said intra-venous tube at one end of the major axis and to said sheath at the other end of the major axis.

13. The expandable catheter of claim 12 further comprising:
six of said inflators and six of said passages.

14. The expandable catheter of claim 10 further comprising:
said sheath extending outwardly from said shoulder and encasing said inflators to near said tip.

15. The expandable catheter of claim 14 further comprising:
said sheath forming a head slightly inwardly from said tip;
said needle having a plurality of vents proximate said tip;
said sheath having a plurality of vents in registration with the plurality of vents of said needle.

16. The expandable catheter of claim 15 further comprising:
a passage between each pair of adjacent inflators forming when said catheter is in the expanded state;
each of said passages having an equiangular spacing around said intra-venous tube; and,
each of said passages adapted to increase fluid flow rate from that of said needle.

17. An expandable catheter that increases fluid flow rate comprising: a block having a generally cylindrical form, a diameter, and a length perpendicular to the diameter, an inflator port in said block and an opposite intra-venous port in said block, a shoulder having a diameter lesser than that of said block and a length lesser than that of said block, said shoulder being coaxial with said block, said shoulder located opposite said inflator port and said intra-venous port; a hollow needle with a tip and an opposite base, said needle extending axially through said block and outwardly from said shoulder; an intra-venous tube concentric and coaxial with said needle and outwardly from said shoulder; at least three inflators along said needle extending outwardly from said shoulder towards said tip, said inflators having an equiangular spacing around said intra-venous tube, each of said inflators having an elongated, hollow, slender form, a flat cross section when said catheter is in a flat state and an elliptical cross section when said catheter is in an expanded state, the elliptical cross section having a major axis and a minor axis of lesser length than the major axis, each of said inflators having its major axis oriented radially outwardly from said intra-venous tube; a sheath extending outwardly from said shoulder over said inflators towards said tip and outwardly from said intra-venous tube, said sheath having a conical portion fitting upon said shoulder, said sheath encasing said inflators to near said tip, each of said inflators joining to said intra-venous tube at one end of the major axis and to said sheath at the other end of the major axis; said intra-venous port having fluid communication into said needle, said inflator port having gaseous communication into said inflators, and said shoulder having fluid communication to said needle; said intra-venous tube being within said inflators and within said sheath; said sheath forming a head slightly inwardly from said tip; said needle having a plurality of vents proximate said tip and said sheath having a plurality of vents in registration with the plurality of vents of said needle; and, wherein said catheter transitions from the flat state having said inflators flat and adjacent to said intra-venous tube to the expanded state having said inflators enlarged radially outwardly from said intra-venous tube; said sheath encasing said inflators when said catheter is in the expanded state; a passage between each pair of adjacent inflators forming when said catheter is in the expanded state, each of said passages having an equiangular spacing around said intra-venous tube and each of said passages adapted to increase fluid flow rate from that of said needle.

18. The expandable catheter of claim 17 further comprising:
six of said inflators and six of said passages.

* * * * *